US011169094B2

(12) United States Patent
Husmann et al.

(10) Patent No.: US 11,169,094 B2
(45) Date of Patent: Nov. 9, 2021

(54) TEST FOR DETERMINING THE PHOSPHATE CONCENTRATION

(71) Applicant: Axagarius GmbH & Co. KG, Dueren (DE)

(72) Inventors: Ralph Husmann, Dueren (DE); Lucas Mertens, Eschweiler (DE)

(73) Assignee: Axagarius GmbH & Co. KG, Dueren (DE)

(*) Notice: Subject to any disclaimer, the term of this patent is extended or adjusted under 35 U.S.C. 154(b) by 261 days.

(21) Appl. No.: 16/430,829

(22) Filed: Jun. 4, 2019

(65) Prior Publication Data
US 2019/0376904 A1 Dec. 12, 2019

(30) Foreign Application Priority Data
Jun. 7, 2018 (DE) ...................... 10 2018 209 082.3

(51) Int. Cl.
*G01N 21/78* (2006.01)
*G01N 33/18* (2006.01)

(52) U.S. Cl.
CPC ............ *G01N 21/78* (2013.01); *G01N 33/18* (2013.01)

(58) Field of Classification Search
CPC ................................ G01N 21/78; G01N 33/18
See application file for complete search history.

(56) References Cited

U.S. PATENT DOCUMENTS

| | | | |
|---|---|---|---|
| 5,858,797 A | 1/1999 | Evtodienko et al. | |
| 6,030,842 A | 2/2000 | Peachey-Stoner | |
| 9,052,303 B2 | 6/2015 | Radmacher et al. | |
| 10,285,401 B2 | 5/2019 | McSherry et al. | |
| 2003/0180183 A1* | 9/2003 | Fukuoka | G01N 33/54393 422/400 |
| 2007/0092972 A1* | 4/2007 | Xiao | G01N 21/78 436/103 |
| 2008/0206879 A1* | 8/2008 | Malone | G01N 21/78 436/60 |
| 2011/0217573 A1* | 9/2011 | Kritzer | H01M 10/484 429/61 |
| 2016/0187309 A1* | 6/2016 | Kang | G01N 31/222 436/41 |

(Continued)

FOREIGN PATENT DOCUMENTS

| | | |
|---|---|---|
| DE | 69805804 T2 | 2/2003 |
| DE | 102008057471 B3 | 5/2010 |

(Continued)

OTHER PUBLICATIONS

Murphy, J. & Riley J.P., "A Modified Single Solution Method for the Determination of Phosphate in Natural Waters", Analytica Chimica Acta 27: 31-36 (1962).

(Continued)

*Primary Examiner* — Jennifer Wecker
*Assistant Examiner* — Kathryn Elizabeth Limbaugh
(74) *Attorney, Agent, or Firm* — The Webb Law Firm

(57) ABSTRACT

The present invention relates to a device for determining the concentration of inorganic phosphate, especially orthophosphate, where said device is a test matrix including a molybdate salt, a solid acid, a PVP derivative, and a mixture of at least two different chromogenic reducing agents. In addition, the invention relates to a process for increasing the sensitivity of a test device.

19 Claims, 7 Drawing Sheets

(56) References Cited

U.S. PATENT DOCUMENTS

2017/0209313 A1\* 7/2017 Letourneau ............ A61F 13/42

FOREIGN PATENT DOCUMENTS

DE 102016202428 A1 8/2017
WO 2017044806 A1 3/2017

OTHER PUBLICATIONS

Bartels et al., "A Kinetic Study on the Influence of the Parameters in the Determination of Inorganic Phosphate by the Molybdenum Blue Reaction," Clinica Chimica Acta, 1975, pp. 135-144, vol. 61.

\* cited by examiner

| Entry | Test strip | Concentration (mg/l) | | | | | |
|---|---|---|---|---|---|---|---|
| | | 0.0 | 0.25 | 0.5 | 1.0 | 3.0 | 5.0 |
| 1 | Hach | pink | pink | pink | pink | slightly pink-blue | slightly pink-blue |
| 2 | Merck MQuant (with additional reagent) | light yellow | light yellow | light yellow | light yellow | light yellow | light yellow |
| 3 | Merck Reflectoquant (with additional reagent) | white | white | white | white | white | very light green |
| 4 | MN (with additional reagent) | very light yellow-green | very light yellow-green | very light yellow-green | very light yellow-green | very light yellow-green | light yellow-green |
| 5 | MN (strip to be protected) | white-gray | very light green | light green | green-blue | intensive green-blue | dark green-blue |

Figure 2

| Entry | Composition | Weight | Bonding method | Absorption capacity (g/g)[a] | Absorption capacity (g/m²) | Optical absorption capacity[b] |
|---|---|---|---|---|---|---|
| 1 | 100% PES[a] | 100 g/m² | mechanically | 3.9 | 390 | 4 |
| 2 | 100% PES | 130 g/m² | mechanically | 4.1 | 533 | 2 |
| 3 | 100% PES | 150 g/m² | mechanically | 2.9 | 435 | 2 |
| 4 | 100% PES | 120 g/m² | thermally | 1.5 | 180 | 5 |
| 5 | 100% PES | 160 g/m² | thermally | 1.4 | 224 | 6 |
| 6 | 100% PES | 100 g/m² | mechanically + thermally | 3.7 | 370 | 1 |
| 7 | 100% PES | 150 g/m² | mechanically + thermally | 3.6 | 540 | 1 |
| 8 | 80% PES / 20% CV[c] | 100 g/m² | chemically | 2.6 | 260 | 4 |
| 9 | 70% PES / 30% CV | 100 g/m² | mechanically + thermally | 3.5 | 350 | 1 |
| 10 | 70% PES / 30% CV | 125 g/m² | mechanically + thermally | 3.1 | 388 | 1 |
| 11 | 70% PES / 30% CV | 150 g/m² | mechanically + thermally | 3.2 | 480 | 1 |
| 12 | PES / CV | 75 g/m² | chemically | 3.5 | 263 | 2 |
| 13 | PES / CV | 100 g/m² | thermally | 1.3 | 130 | 3 |
| 14 | PES / CV | 100 g/m² | thermally + chemically | 3.4 | 340 | 4 |
| 15 | PES / CV | 130 g/m² | thermally + chemically | 2.9 | 377 | 2 |

[a] Absorption capacity determined through the starting weight of the non-woven fabric and subsequent weighing again after immersion into FD water and squeezing off on an impregnation machine, [b] scale of 1-6 (1 = very good, 6 = fail), [c] non-woven is not stable (basic color dark green after some weeks)

Figure 3

| Entry | Designation | $M_w$(PVP) | Result |
|---|---|---|---|
| 1 | without PVP | - | only from 5 mg/L $PO_4^{3-}$ |
| 2 | N-methyl-2-pyrrolidone | - | n. r.[a] |
| 3 | 1-dodecyl-2-pyrrolidone | - | n. r. |
| 4 | PVPP[b] | - | insoluble (in water) |
| 5 | PVP K25 | 24,000 g/mol | weak reaction |
| 6 | PVP K40 | 40,000 g/mol | good color grading |
| 7 | PVP K90 | 360,000 g/mol | false positive result[c] (poor solubility) |
| 8 | PVP K40 / PVP K90 | - | weak reaction |
| 9 | PVA[d]-Co-PVP 7:3 | 50,000 g/mol | weak reaction |
| 10 | PVA-Co-PVP 3:7 | 50,000 g/mol | weak reaction |
| 11 | Luviskol[e] | - | n. r. |

[a] no reaction, [b] poly(vinylpolypyrrolidone) - cross-linked - particle size 110 μm, [c] The zero value already shows a green-blue color, [d] polyvinylacetate, [e] polyvinylcaprolactam

Figure 4

| Entry | Acid | pH value of impregnation solution | Result |
|---|---|---|---|
| 1 | oxalic acid | 1.0 | n. r. |
| 2 | tartaric acid | - | n. r. |
| 3 | cyclamic acid | 1.48 | good reaction color (from 0.5 mg/l) |
| 4 | methylamidosulfonic acid[a] | 1.0 | distinguishability from 3 mg/l |
| 5 | amidosulfuric acid | 1.6 | distinguishability from 1 mg/l |
| 6 | MOPS[b] (+ HCl) | 1.5 | n. r.[c] |
| 7 | MES[d] (+ HCl) | 1.5 | n. r.[c] |
| 8 | polystyrenesulfonic acid (+ HCl) | 1.0 | n. r.[c] |
| 9 | polyacrylic acid + cyclamic acid (+ HCl) | 0.75 | reaction color from 3 mg/l |
| 10 | p-toluenesulfonic acid + cyclamic acid | - | reaction color from 1 mg/l |
| 11 | polystyrenesulfonic acid + cyclamic acid (+ HCl) | 1.0 | not applicable |
| 12 | ascorbic acid + cyclamic acid | | reaction color from 3 mg/l |
| 13 | cyanuric acid + cyclamic acid | - | not applicable |

[a] hardly soluble, [b] 3-(N-morpholino)propanesulfonic acid, [c] very weak reaction,
[d] 2-(N-morpholino)ethanesulfonic acid

Figure 5

| Entry | Reducing agent | Result/color | Remark |
|---|---|---|---|
| 1 | Leuko Bindschedler's green | green-blue | - |
| 2 | Leuko malachite green + TMB[a] | green | from 3 mg/l |
| 3 | Leuko crystal violet + TMB | green | from 3 mg/l |
| 4 | Ascorbic acid | n. r. | - |
| 5 | Syringaldazine + vanillinazine | n. r. | - |
| 6 | Aminophenol | n. r. | - |
| 7 | Zinc | n. r. | - |
| 8 | Leuko Bindschedler's green + TMB | green-blue | from 0.5 mg/l |
| 9 | Leuko Bindschedler's green + ascorbic acid | blue | from 3 mg/l |
| 10 | LBG[b] + benzoyl-leuko-methylene blue | green-blue | from 1 mg/l |
| 11 | LBG + 1,2-phenylenediamine | green-blue | from 3 mg/l |
| 12 | LBG + 1,3-phenylenediamine | green-blue | from 1 mg/l |
| 13 | LBG + 1,4-phenylenediamine | green-blue | from 3 mg/l |
| 14 | LBG + o-toluidine | green-blue | from 3 mg/l |

[a] 3,3',5,5'-tetramethylbenzidine, [b] leuko Bindschedler's green

Figure 6

| Entry | Reducing agent | Concentration (mg/l $PO_4^{3-}$) | | | | | |
|---|---|---|---|---|---|---|---|
| | | 0.0 | 0.25 | 0.5 | 1.0 | 3.0 | 5.0 |
| 1 | LBG[a] | green-white | green-white | light green | green-blue | intensive green-blue | intensive green-blue |
| 2 | TMB[b] | green-white | green-white | light green | green-blue | intensive green-blue | intensive green-blue |
| 3 | LBG / TMB | white | very light green | light green | green-blue | intensive green-blue | dark green-blue |
| 4 | LBG / LMG[c] | green-white | very light green | light green | green-blue | intensive green-blue | intensive green-blue |
| 5 | LBG / LKV[d] | green-white | very light green | light green | green-blue | intensive green-blue | intensive green-blue |
| 6 | LBG/1,3-phenylenediamine | white-gray | white-gray | very light green | light green | green-blue | intensive green-blue |
| 7 | LBG / MDA[e] | white-gray | white-gray to very light green | very light green | light green | green-blue | intensive green-blue |
| 8 | LMG / TMB | white-gray | white-gray | very light green | light green | green-blue | green-blue |
| 9 | LKV / TMB | white-gray | white-gray | very light green | light green | green-blue | green-blue |

[a] leuko Bindschedler's green, [b] 3,3',5,5'-tetramethylbenzidine, [c] leuko malachite green, [d] leuko crystal violet, [e] 4,4'-methylene-N,N-bis(dimethylaniline)

Figure 7

TEST FOR DETERMINING THE PHOSPHATE CONCENTRATION

CROSS-REFERENCE TO RELATED APPLICATION

This application claims priority to German Patent Application No. 10 2018 209 082.3 filed Jun. 7, 2018, the disclosure of which is hereby incorporated by reference in its entirety.

BACKGROUND OF THE INVENTION

Field of the Invention

The present invention relates to a device for determining the concentration of inorganic phosphate, especially orthophosphate, wherein said device is a test matrix comprising a molybdate salt, a solid acid, a PVP derivative, and a mixture of at least two different chromogenic reducing agents. In addition, the invention relates to a process for measuring the phosphate concentration using the device according to the invention, and a process for increasing the sensitivity of a test device.

Technical Considerations

Phosphorus is used in numerous industrial products. It arrives in the environment, for example, through fertilizers and detergents, mostly being in the form of orthophosphate or polyphosphate. The importance of the plant nutrient phosphorus is due to its eutrophication potential. Further, the analytical determination of orthophosphate is of great importance also in other fields in addition to environmental analytics, such as in clinical and agricultural analytics.

In the clinical field, the determination of phosphate in body fluids, such as urine or blood, is important, because the detection of increased phosphate concentrations in such fluids allows for the diagnosis of diseases, such as uremia or chronic renal diseases, i.e. diseases associated with phosphate retention.

Ultimately, the determination of phosphate is also necessary in the private field in the quality control of aquarium water. The determination of dissolved inorganic phosphate in aqueous liquids is generally performed by the method according to Murphy and Riley (1962) (Murphy, J. & Riley, J. P., 1962. A modified single solution method for the determination of phosphate in natural waters. Analytica Chim. Acta 27: 31-36). In this detection, the orthophosphate present in the aqueous liquid forms molybdatophosphoric acid together with molecules of hexamolybdic acid in a pH range around 1.5. This reaction is catalytically accelerated by polyvinyl pyrrolidone. A reducing agent (e.g., ascorbic acid) as part of the mixed reagent reduces the heteropoly acid by one or two equivalents to form blue color complexes, representing bright blue molybdenum(VI)-molybdenum(IV) mixed oxides as so-called "molybdenum blue". The absorbance of the color complex is proportional to the concentration of the phosphoromolybdate complex and thus to the concentration of phosphate in the sample. When performed as a quick test, the reaction components are contained in a support matrix, and the color change of the test matrix is detected visually after soaking with the liquid to be determined. In contrast to an automated liquid-only assay, the methods based on a test matrix from the prior art are relatively robust as long as they have a detection limit of 3.0 mg/l of orthophosphate.

The U.S. Pat. No. 5,858,797 relates to a colorimetric phosphate assay and discloses the use of a chromogenic reducing agent, or "a reducing dyestuff". Accordingly, the redox reaction not only produces the molybdenum blue complex, but also converts the reducing agent, which is in its leuko form, to its colored oxidation form, resulting in a more pronounced color change. The process disclosed therein requires an additional inert dye, such as malachite green or Ponceaus S (column 2, line 33). Accordingly, for a reproducible result in a test based on a test matrix, it is necessary for such an inert dye to dissolve quickly and completely to increase the measuring sensitivity.

One disadvantage resides in the fact that additional reagents are necessary in many quick tests and, in particular, in the particularly sensitive quick tests. Such additional reagents are classically strongly acidic mineral acids, such as nitric acid, which are added to the sample to be measured in a first step, and the test method can be performed only after this mixture has been formed. Thus, the measuring method becomes more error-prone and time-consuming and requires highly corrosive liquids to be handled.

Therefore, there is a need for improved analytical methods and devices for determining the phosphate concentration with a high sensitivity.

Therefore, it is an object of the invention to improve a generic test device or test method for determining the phosphate concentration in such terms that it is improved with respect to at least one of the disadvantages mentioned above.

SUMMARY OF THE INVENTION

According to the invention, this object is achieved by providing a test device for determining the concentration of inorganic phosphate in a liquid sample, wherein said test device contains a support matrix serving as a support for the liquid sample, the detection reagents and the detection reaction, wherein said support matrix comprises:
  a) at least one molybdate salt;
  b) at least one acid that is solid at room temperature;
  c) a polyvinyl pyrrolidone derivative; and
  d) a combination of at least two different chromogenic reducing agents.

The test device according to the invention combines several critical advantages over the orthophosphate test devices known from the prior art.

As the inventors found out, the presence of a combination of two different chromogenic reducing agents results in a significant improvement of the detection limit. Thus, the orthophosphate can be detected already in a concentration of 0.25 mg/l.

Thus, low concentrations as are relevant to many applications (such as aquarium water tests) become unequivocally detectable.

Since the test device is based on a quick redox reaction with a direct color detection, it represents a direct and very quick detection method (so-called "quick test"). In addition, the test device according to the invention is simple to use and interpret and does not require any additional measuring devices. This allows it to be applied just in the private field, because a user without a technical or laboratory-analytical education can also perform a quick and reliable visual detection.

Also, in contrast to many other orthophosphate test systems, the device according to the invention does not require any additional reagent that has to be mixed in advance with the sample to be measured, then measuring this mixture with the actual test device. In the device according to the invention, the orthophosphate-containing sample can be measured with the test device directly and without a pretreatment.

Further, the device according to the invention can achieve the high measuring sensitivity even without the addition of an inert dye.

The test device allows for a selective determination, i.e., one that is aimed only at orthophosphate.

By pretreating the sample accordingly, the detection can be extended to other phosphate species, such as organic phosphates, diphosphates, metaphosphates, or polyphosphates.

The test device also has sufficient stability and does not require cooling if the conventional reagents are used.

By selecting suitable ingredients, the robustness of the test device allows for some variability of the sample to be analyzed (e.g., sample pretreatment not required) and/or of other defined physical parameters during the measuring process, nevertheless yielding reproducible and standardizable results.

Thus, it meets all the requirements that an analytically employed test device or test method have to meet, and thus can also be validated.

The test device can be prepared with commercially available substances in a simple manner and, in addition, at low cost.

The test device can be integrated into established test systems without additional effort.

BRIEF DESCRIPTION OF THE DRAWINGS

In the Figures:

FIG. 2 shows the results of the measurement from Example 2, comparing the test device according to the invention with four commercially available test strips. What is shown is the visually detected color change of the test strips after immersion into a solution with 0.0, 0.25, 0.5, 1.0, 3.0 and 5.0 mg/l of phosphate.

FIG. 3 shows the results of the measurement from Example 3 with the test device according to the invention with variation of the support matrix material, wherein 15 different non-woven fabrics were tested comparatively.

FIG. 4 shows the results of the measurement from Example 4 with the test device according to the invention with variation of the PVP derivative, wherein 10 different polymers were tested comparatively.

FIG. 5 shows the results of the measurement from Example 5 with the test device according to the invention with variation of the solid acid, wherein 13 different acids or combinations of acids were tested comparatively.

FIG. 6 shows the results of the first test series from Example 6 with the test device according to the invention with variation of the reducing agent, wherein 14 different reducing agents or mixtures thereof were tested comparatively.

FIG. 7 shows the results of the second test series from Example 6 with the test device according to the invention with variation of the reducing agent, wherein 9 different reducing agents or mixtures thereof were tested comparatively.

DESCRIPTION OF THE INVENTION

Figure 1:
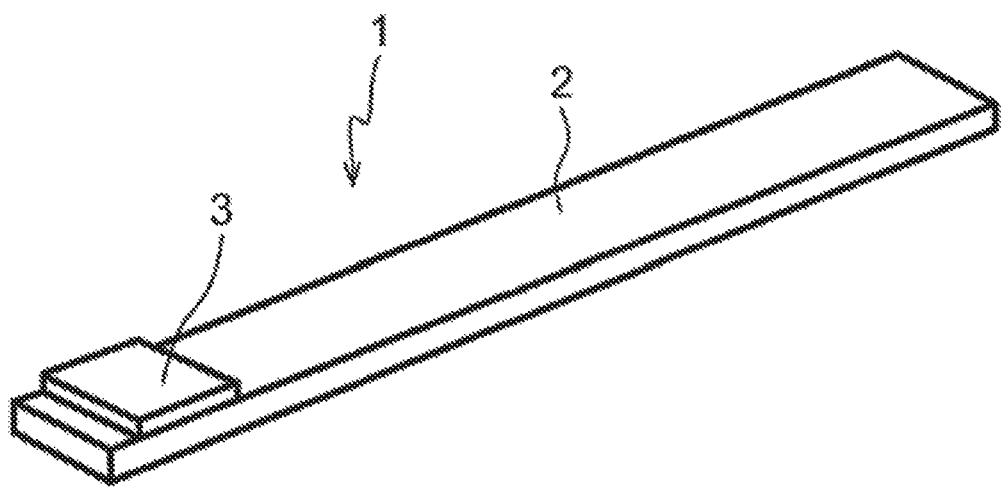
FIG. 1 shows a test device designed as a test strip comprising a plastic strip 2 as the support, to which a support matrix 3 is attached. The support matrix contains the detection reagents necessary for the determination, which are preferably cyclamic acid, PVP K40, ammonium molybdate, leuko Bindschedler's green, and 3,3',5,5'-tetramethylbenzidine.

The test device is based on the formation of a molybdatophosphoric acid complex with subsequent reduction to form a total of three colored molecular species:
1. molybdenum blue
2. colored oxidized form of a first chromogenic reducing agent; and
3. colored oxidized form of a second chromogenic reducing agent.

As a working hypothesis, it is considered that it is the formation of a total of three colored molecular species that leads to a particularly sensitive measuring method.

The coloring of the test matrix can be evaluated with different methods. In the simplest form, it is compared with a corresponding color on a standard color chart, in which the individual color values are assigned to particular phosphate concentrations.

In another embodiment, the test device allows for the use of at least one inert dye. This inert dye is tuned to the chromogenic reducing agent or the combination thereof with their color changes, and allows for a better detection of the color change by providing a constant background coloring. Thus, when the change goes from colorless to green, the use of a yellow-orange inert dye is advantageous.

According to the invention, the inert dye is to be provided in the same section as the chromogenic reducing agent. This can be realized in different ways, for example:
(a) The inert dye can be applied to the support itself, or provided by a colored support.
(b) The inert dye can be incorporated into the support matrix.
(c) The support matrix itself can be colored.
(d) The test device can have a separate colored layer below the support matrix.

Preferably, one inert dye is employed. However, two, three or even more inert dyes may also be employed in order to achieve a colorfulness that is optimal for the system.

Further preferably, the support matrix contains one inert dye.

In one embodiment of the invention, at least one inert dye is selected from the group containing tartrazine, Neozapon yellow, Ponceau S, Sunset yellow, and nitrazine yellow, wherein said inert dye is preferably Sunset yellow.

In an alternative embodiment, which is also preferred, the support matrix does not include an inert dye. As set forth above, the device according to the invention enables an excellent measuring sensitivity to be achieved already by its combination of two different chromogenic reducing agents. Therefore, an inert dye is not necessary in the basic design.

Said at least one molybdate salt contained in the test matrix may be any water-soluble salt as long as it is compatible with the other detection reagents and the test matrix itself. The molybdate salt is preferably selected from the group consisting of ammonium molybdate, sodium molybdate, calcium molybdate, and potassium molybdate, ammonium molybdate being particularly preferred. The concentration of the molybdate salt in the impregnation solution is from 2 to 50 g/l, preferably from 5 to 15 g/l, and more preferably from 7 to 11 g/l.

Further preferably, the support matrix contains one molybdate salt.

In order to form a strongly acidic pH, the test matrix also contains at least one solid acid. The solid acid of the test device serves for complex formation between the phosphate and molybdate and allows the phosphate to be quantified through the formation of a strongly acidic pH value. Being a solid, it will not volatilize, but remains as a solid in the support matrix and allows for a formulation that is stable in the long term.

Conveniently, the acid is an organic acid.

Said at least one solid acid is preferably an organic amidosulfonic acid.

In a preferred embodiment, the acid is selected from the group consisting of methylamidosulfonic acid, amidosulfonic acid, and cyclamic acid, cyclamic acid being preferred.

Preferably, one acid is employed. However, two, three or even more acids may be employed, for example, for digesting polyphosphates in the starting solution with hydrolysis to form orthophosphate.

In one embodiment of the invention, the solid acid is present as a pure acid, i.e., it is not supplemented by adding its conjugate base to form a buffer system.

According to the invention, the test device includes polyvinyl pyrrolidone, which acts as a catalyst and wetting agent. The polyvinyl pyrrolidone contained in the test matrix may be any water-soluble PVP derivative as long as it is compatible with the other detection reagents and the test matrix itself. Preferably, the polyvinyl pyrrolidone (PVP) derivative has a K value of from 25 to 90, more preferably being PVP K40. The concentration of the polyvinyl pyrrolidone in the impregnation solution is from 20 to 120 g/l, preferably from 30 to 80 g/l, and more preferably from 40 to 60 g/l.

According to the invention, two different chromogenic reducing agents are used in the test device, wherein such reducing agents are employed in their reduced leuko form, so that they are converted to the oxidized colored form in the redox reaction. The reducing agent contained in the test matrix may be any chromogenic reducing agent that is soluble in water and/or alcohol as long as it is compatible with the other detection reagents and the test matrix itself, and allows the reduction of the molybdatophosphoric acid because of its redox potential. The concentration of said chromogenic reducing agent in the impregnation solution is from 0.25 to 5 g/l, preferably from 0.5 to 2.5 g/l, and more preferably from 0.7 to 2 g/l.

In a preferred embodiment, the different chromogenic reducing agents occurring in the combination are selected from the group consisting of leuko Bindschedler's green (LBG), leuko malachite green (LMG), leuko crystal violet (LKV), 3,3',5,5'-tetramethylbenzidine (TMB), benzoyl-leuko-methylene blue, 4,4'-methylene-N,N-bis(dimethylaniline) (MDA), 1,2-phenylenediamine, 1,3-phenylenediamine, and 1,4-phenylenediamine.

In the impregnation solution, the LBG is preferably in a concentration of from 0.1 to 2.0 g/l, more preferably from 0.2 to 1.8 g/l, and especially from 0.5 to 0.7 g/l.

In a preferred embodiment of the invention, the test matrix of the test device has a combination of exactly two chromogenic reducing agents.

In a particularly preferred embodiment, the combination of exactly two chromogenic reducing agents is one of the following combinations:
  a) LBG and TMB
  b) LBG and benzoyl-leuko-methylene blue
  c) LBG and 1,3-phenylenediamine
  d) LBG and MDA
  e) LBG and LMG
  f) LBG and LKV
  g) LMG and TMB, or
  h) LKV and TMB.

In a specific embodiment, the test matrix has a combination of LBG and TMB. The molar ratio of LBG to TMB therein is from 10:1 to 1:10, preferably from 5:1 to 1:2, and more preferably 2:1.

In another embodiment, the support matrix also contains at least one surfactant in order to facilitate the wetting of the test matrix. In a particular embodiment, a combination of non-ionic and anionic surfactants is employed.

In one embodiment, said at least one non-ionic surfactant is selected from the group consisting of fatty alcohol ethoxylates (FAEO), such as Brij35, fatty alcohol propoxylates (FAPO), alkylglucosides, such as Tween 20, alkylpolyglucosides (APG), octylphenolethoxylates, and Nonidet P40. In a preferred embodiment, said non-ionic surfactant is Nonidet P40.

In one embodiment, said anionic surfactant is selected from the group consisting of sodium dodecylsulfate, ammonium dodecylsulfate, sodium lauryl ether sulfate (SLES), sodium myristyl ether sulfate, sodium dioctylsulfosuccinate, perfluorooctanesulfonate (PFOS), perfluorobutanesulfonate, and linear alkylbenzenesulfonates. In a preferred embodiment, said anionic surfactant is sodium dodecylsulfate.

In one embodiment, one detection reagent or several detection reagents or even all detection reagents are immobilized in the support matrix.

In one embodiment of the invention, the test device is designed as a test strip or test tape, and/or it has such a design that it can be included in an integrated test system.

The test strip can be prepared from a wide variety of materials. Preferred are waterproof materials, such as plastic materials. The test strip preferably consists of polyvinyl chloride or polyethylene.

In another embodiment, the test device may have further support matrices.

By one or more additional support matrices that are also prepared for determining the phosphate concentration, different measuring ranges can be covered.

Conveniently, the additional support matrices may also be designed for the determination of different target analytes. Thus, in the aquarium field, it is common to determine further parameters, such as the pH, nitrate content, nitrite content, carbonate hardness, total hardness, and chlorine content.

The support matrix according to the invention is conveniently made of a liquid-absorbing material. Because of this property, the material takes up a defined amount of liquid to be analyzed, retaining it, and thus allows the solid detection reagents to be solubilized by the liquid, followed by the detection reaction in the support matrix.

Numerous materials and structures that are suitable as a support matrix are known to the skilled person from the prior art, and they can purposefully select them depending on the test principle.

Preferably, the support matrix is a liquid-absorbing material. This material is preferably selected from the group containing filter paper, non-woven, glass fiber, porous polymer material made of polysulfone, polyester, nylon, nitrocellulose, PVDF, polycarbonate, a non-woven or non-woven fabric being particularly preferred.

In a preferred embodiment, the support matrix is a non-woven fabric. Non-woven fabric are inexpensive and highly absorptive and can be impregnated simply (by soaking and subsequent drying) with the test reagents.

The non-woven used in the device according to the invention may be constituted of all possible kinds of fibers.

Known kinds of fibers include mineral fibers, such as glass, asbestos, mineral wool, animal fibers, such as silk and wool, vegetable fibers, such as cotton, and chemical fibers. With the chemical fibers, a distinction is made between fibers of natural polymers, such as cellulose, and fibers of synthetic polymers. According to the invention, the latter are also referred to as plastic fibers. Examples of chemical fibers of synthetic polymers include the polyamides PA 6.6 (Nylon®), PA 6.0 (Perlon®), polyester (PES), such as polyethylene terephthalate (PET), and polybutylene terephthalate (PBT), polyvinyl chloride (PVC), polypropylene (PP), polyethylene (PE), polyimide (PI), polyamideimide (PAI), polyphenylene sulfide (PPS), aramid, polyacrylonitrile (PAN), polytetrafluoroethylene (PTFE).

For bonding the fibers of the non-woven into a non-woven fabric, different methods are known to the skilled person. These include mechanical methods, such as needle punching or water jet bonding, chemical methods, such as by adding binders, or thermal methods, for example, softening in a suitable gas stream, between heated rollers, or in a steam flow. Preferably, the non-woven is bonded mechanically (e.g., by needle-punching as a needle-punched non-woven) or thermally, or the bonding is effected by a combination of mechanical and thermal methods. It has been found that mechanically and/or thermally bonded non-woven fabrics show a better color reaction as compared to the chemically or chemically and thermally bonded non-woven fabrics, which may be due to the poorer suction behavior of the latter.

According to a preferred embodiment, the non-woven fabric has a water absorption coefficient of from 500 to 1000 $kg/m^2\sqrt{h}$ and more preferably of from 700 to 900 $kg/m^2\sqrt{h}$.

In a specific embodiment, the non-woven (or accordingly the bonded non-woven fabric) consists of polyester (PES) and/or viscose (CV). As set forth in Example 3, these materials are particularly advantageous with respect to a high measuring sensitivity.

In one embodiment, the support matrix has a one-layer structure, so that all the detection reagents are contained in this one layer. In an alternative embodiment, the support matrix may be constituted of two or more layers. Thus, for example, the individual layers may have different absorbencies or absorbing capacities for liquids, so that the liquid sample can be taken up more selectively, and also bleeding of the support matrix can be prevented. In addition, this allows for a spatial separation of the different detection reagents, so that chemically/physically non-compatible detection reagents can be used, or the liquid sample intruding from outside can react sequentially with the detection reagents while it penetrates the individual layers.

Further, the support matrix may also have a region designated as a "waste pad", which takes up the liquid that has passed through the support matrix. In this region, for example, an absorbing mat or a non-woven, a blotting or filter paper or the like may be provided.

In a particular embodiment, the invention provides a test device for determining the concentration of orthophosphate, wherein the support matrix includes:
a) cyclamic acid
b) PVP K40
c) ammonium molybdate
d) leuko Bindschedler's green
e) 3,3',5,5'-tetramethylbenzidine.

In a particularly preferred embodiment, the above mentioned support matrix is a non-woven fabric applied to a test strip.

In a second aspect, the invention provides a test method for determining the concentration of orthophosphate in a liquid sample using the test device according to the invention, the test method comprising the following steps:
a) soaking the support matrix with the liquid sample, preferably by dipping into the sample;
b) removing any excess sample material from the support matrix, preferably by withdrawing the test strip from the liquid sample; and optionally shaking off or stripping off excess liquid sample;
c) optionally incubating the test strip for at least 5 seconds, preferably at room temperature;
d) visually detecting the color value of the support matrix, preferably by comparison with a color standard.

In a preferred embodiment, this liquid sample is an aqueous solution.

In one embodiment, the visual detection of the color value of the support matrix can be effected by means of an evaluation device. This device can be a spectrometer, or just a device comprising a camera. A mobile device with a camera is preferred. Such mobile devices include, for example, smartphones, tablet computers, digital cameras connected to a computer, or small portable computers with a built-in camera. In a further preferred embodiment, an application software for recording and evaluating the color value is stored on the device and can also be executed thereon. A corresponding measuring system for evaluating colorimetric assays is disclosed, for example, in the German Patent Application DE 10 2016 202 428.0.

In a third aspect, the invention relates to the use of a combination of two different chromogenic reducing agents for enhancing the sensitivity of an analytical method based on a support matrix and on a redox reaction.

This analytical method is preferably a phosphate test method.

Definitions

Within the scope of the present invention, a "test device" means a support-based tests for medical and non-medical purposes. In such support-based tests, detection reagents are embedded in the support matrix of a support, which is contacted with the liquid sample, wherein said support matrix serves as a support for the examination material and as a support for the detection reaction. When the target analyte, i.e., orthophosphate ions, is present, the reaction of the liquid sample with the reagents leads to a color change, which can be evaluated visually or by means of a device, for example, by transmission photometry, reflection photometry, or fluorescence photometry.

According to the invention, the "phosphate" measured with the test device means all phosphate species that are derived from orthophosphoric acid and thus include dihydrogenphosphate ($H_2PO_4^-$), monohydrogenphosphate ($HPO_4^{2-}$) and phosphate ($PO_4^{3-}$), in addition to orthophosphoric acid.

A "chromogenic reducing agent" means a reducing agent that is colorless or almost colorless (cream, light yellow) in its reduced form and is converted to a colored oxidized form by the redox reaction.

According to the invention, a "solid acid" means an acid that is in a solid state of matter at room temperature. This may be either an organic acid or an inorganic acid.

The K value represents a classification common in the plastics industry and is in direct relationship with the average molar mass of the polymer. Thus, indirect conclusions can be made from the K value to the degree of polymerization and thus the chain length. The K value, also referred to as "intrinsic viscosity", is determined by viscosity measurements of polymer solutions and is often used in the technical field for determining the molar mass of polymers, such as PVC. For constant measuring conditions in terms of solvent, solvent concentration and temperature, the K value is only dependent on the average molar mass of the polymers examined. It is calculated through the relationship K value=1000·k according to the Fikentscher equation, in which: $\eta_r$=relative viscosity (dynamic viscosity of the solution/dynamic viscosity of the solvent), and c=mass concentration of the polymer in the solution in g/cm$^3$.

Fikentscher Equation:

$$K = 1000 \cdot k = 1000 \cdot \frac{1.5 \lg\eta_r - 1 + \sqrt{1 + \left(\frac{2}{c} + 2 + 1.5 \lg\eta_r\right) \cdot 1.5 \lg\eta_r}}{150 + 300\, c}$$

The determination of the K value is effected in accordance with the standard DIN ISO 1628-1.

According to the invention, an "inert dye" means a dye that does not change its color, or changes it insignificantly, at least in the pH range used in the test (i.e., strongly acidic), and thus enables a constant color-contrasting background.

According to the invention, a "non-woven" means a structure made of fibers of limited length, continuous fibers (filaments) or chopped yarns of any kind and any origin that are joined or bonded together in some way. Excluded therefrom is the crossing or interweaving of yarns, as is done in weaving or knitting. A non-woven with bonded fibers is also referred to as a "non-woven fabric". The non-wovens according to the invention are flexible sheets, meaning that they are flexible, their main structural elements are fibers, especially textile fibers, and they have a relatively low thickness as compared to their length and width.

According to the invention, the term "comprising" also includes the terms "essentially consisting of" and "consisting of", in addition to its literal meaning. Thus, an object that "comprises" especially listed elements may include further elements in addition to the listed ones, or it may not include any further elements, within the meaning of "consisting of".

"Selectivity" means the ability of certain substances to preferentially select one among a number of possibilities offered for reaction. An exclusive selection is referred to as "specificity".

"Sensitivity" means the intensity of change in the response of a measuring signal, divided by the change of the triggering quantity (e.g., the concentration of the target analyte). The sensitivity of an analytical method corresponds to the slope of the calibration curve.

According to the invention, the distinguishable terms of "system precision" (measuring precision) and "method precision" are defined as follows: Measuring precision is a measure of the variations caused by the test device or the analytical device working with it, itself. It is determined by multiple (e.g., six fold) analysis of a standard. The required measuring precision depends on the analytical device. In contrast, method precision describes the random scattering of the analytical results. It is established by a repeated (mostly six fold) performance of the overall analysis, i.e., from the weighing through the sample preparation to the measurement and result (six charges of real samples).

The "stability" of the test device includes storage stability, stability under physical influences, such as heat, light, mechanical stress.

"Accuracy" is a measure of the deviation of the measured value from the correct value (sometimes referred to as the "true" value) because of a bias. The accuracy is generally determined by a comparison with a reference or working standard (target/actual comparison), a comparison with an independent method, possibly a validated one, or by the so-called "spiking" of a sample. If none of the three methods is applicable for particular samples, the following may be accepted as a criterion for accuracy: Selectivity has been proven, linearity exists, and the calibration line goes through the origin.

The "detection limit" is the smallest concentration (amount) of the analyte in the sample that can still be detected qualitatively (yes/no decision). The "limit of determination" is the smallest concentration (amount) of the analyte in the sample that can be determined quantitatively at a given precision and accuracy. The underlying mathematical model and the determination methods are described in DIN 32645.

The "limit of decision" states the concentration (amount) that can be detected with a probability of 50%. Thus, the limit of decision can be considered, in a simplified way, as twice the detection limit.

EXAMPLES

1. Preparation of a Phosphate Test Device

The test strip to be protected can be prepared as follows. Three different impregnation solutions are prepared. For one liter of impregnation solution 1, 72 g of PVP K40 and 24 g of ammonium molybdate are dissolved in 800 ml of fully desalted water (FD water). Subsequently, 200 ml of ethanol is added with vigorous stirring. For the second solution, 57 g of cyclamic acid is dissolved in one liter of FD water. For preparing the third solution, 0.9 g of LBG and 1.8 g of TMB are dissolved in one liter of ethanol.

For impregnation, the corresponding non-woven fabric is immersed into the respective test solution and subsequently dried at an average of 325° C. for about one minute. After trimming the impregnated non-woven fabric to size, the test pad thus obtained can be used to prepare the test strip (see FIG. 1). Thus, the test pad is bonded to a 5.5×95 mm sized PVC strip by means of a hot-melt adhesive, followed by storing dry and dark.

2. Comparative Testing of a Phosphate-Containing Test Solution

In order to determine the sensitivity of the test device as compared to test devices from the prior art, the following five test strips were examined comparatively:
1. AquaChek® phosphates (Hach Company, Loveland, USA)
2. MQuant™ phosphate test (Merck KGaA, Darmstadt, Germany)
3. Reflectoquant® plus phosphate test (Merck KGaA, Darmstadt, Germany)
4. QUANTOFIX® phosphate (MACH EREY-NAGEL, Duren, Germany)
5. inventive test strip according to Example 1.

The test strips were immersed into solutions having an orthophosphate content of 0.25, 0.5, 1.0, 3.0 and 5.0 mg/l and phosphate-free solution in accordance with the respective test instructions, and the color change of the test strips was established.

The Table in FIG. 2 summarizes the color reactions of the above mentioned products in the sought concentration range and compares the color series with the test strip according to the invention. The comparison of the five test strips illustrates that current products (entries 1-4) do not reach the sought sensitivity of <3 mg/l of phosphate. While no color reaction at all is provoked with the MQuant™ test strip from Merck (entry 2) from 0 to 5 mg/l of phosphate, the Reflectoquant® plus phosphate test (entry 3) shows a color reaction from 5.0 mg/l of phosphate. By comparison, both the test strips from Hach (entry 1) and those from MN with an additional reagent (entry 4) show a color reaction from 3 mg/l of phosphate. The test strip according to the invention can detect phosphate in a concentration from about 0.25 mg/l of phosphate (entry 5) and is thus more sensitive by a factor of 12 as compared to the second best test strip AquaChek® from the Hach Company.

3. Comparative Test with Variation of the Material for the Support Matrix

For the development of a highly sensitive phosphate test strip, non-woven fabrics play an important role as support materials. Fifteen different non-woven fabrics with different compositions, weights and bonding methods were tested. The test strips were prepared according to Example 1 and immersed into solutions having an orthophosphate content of 0.25, 0.5, 1.0, 3.0 and 5.0 mg/l and into a phosphate-free solution for testing, and the color change of the test strips was determined.

All the non-woven fabrics are clearly different in weight (and thus the corresponding thickness) and starting material. This determines the absorption performance and the associated amount of chemicals applied to the support material. In principle, heavier non-woven fabrics take up more substance during the impregnation, which favors a highly sensitive test. The haptics of the support material is determined, inter alia, by the bonding principle. Mechanically or thermally bonded non-woven fabrics (entries 1-5 and 13) as well as mechanically and thermally bonded non-woven fabrics mostly show a good color reaction (entries 6, 7, 9-11). In contrast, purely chemically (entries 8 and 12) as well as the thermally and chemically bonded non-woven fabrics often show a poor absorption performance and thus a poor color reaction. The Table in FIG. 3 shows a survey of the tested non-woven fabrics, non-woven fabric 10 (PES/CV with 125 g/m$^2$) with the best properties for the test strip according to the invention from Example 1 being pointed out.

As a relevant parameter, the absorbency was determined experimentally for the 15 non-woven fabrics (see FIG. 3). The absorbency of the non-woven fabric will help determine what amount of reactants remain on the non-woven after the impregnation. The absorption capacity is determined by immersing into FD water followed by squeezing out and using the weight difference. However, since some non-woven fabrics are made of the same material, only differing by the weight, the absorption capacity may also be stated as based on the surface area. It becomes clear that a particular absorption capacity (both in g/g and in g/m$^2$) is necessary to enable a suitable color reaction. This is mainly due to two factors. On the one hand, a sufficient amount of impregnating solution must be applied to the non-woven, and on the other hand, the non-woven must be able to soak up with the solution to be examined so that a color reaction can be provoked. Non-woven fabrics having an absorption capacity of <2 g/g (or <250 g/m$^2$) are clearly too hydrophobic and are thus unsuitable for a highly sensitive test (entries 4, 5 and 13). All the non-woven fabrics having an absorption capacity of at least 3.0 g/g are hydrophilic enough to obtain a color reaction after the impregnation. Although the stated non-woven fabrics having an absorption capacity of from 2.0 to 3.0 g/g are absorptive, they are only conditionally suitable for the phosphate test strip. This is due to not only the absorption capacity, but other parameters as well. For example, the absorption capacity of non-woven No. 8 of 2.6 g/g is rather high, but because of chemical bonding and the binder that is contained thereby, this non-woven is worse than a mechanically and/or thermally bonded non-woven. The same applies to non-woven No. 15. The non-woven No. 10 yields the best color series in the experiments. As seen already in the information provided by the manufacturer, all the parameters are found in the medium range.

The optical absorption capacity stated in the last column of the Table is an estimation of the water absorption performance of the non-woven. All non-woven fabrics are immersed in water for the same duration. It is confirmed thereby that the hydrophobic non-wovens absorb water clearly more slowly, or not at all. The non-woven fabrics that have a very high optical absorption capacity mostly also exhibit a good color reaction in an experiment on a small scale.

4. Comparative Test with Variation of the PVP Derivative

As described in the application, the test reaction is optimized by the presence of polyvinyl pyrrolidone (briefly PVP). On the one hand, the PVP serves as a wetting agent, and on the other, it is important to the reaction as such.

Nine different PVP derivatives and, in addition, a caprolactam are tested. A test strip without PVP was prepared as a zero control (No. 1). The test strips were prepared in accordance with Example 1 and immersed into solutions with an orthophosphate content of 0.25, 0.5, 1.0, 3.0 and 5.0 mg/l and into a phosphate-free solution for testing, and the color change of the test strips was determined.

The Table in FIG. 4 shows the PVP derivatives employed and the different average molecular weights that were employed. Although a color reaction is obtained when no PVP is used, it occurs only at about 5 mg/l of phosphate (entry 1). Further experiments show that no reaction occurs with NMP (entry 2) or with 1-dodecyl-2-pyrrolidone (entry 3). While cross-linked PVP (entry 4) is not soluble in water, all the other PVP variants show a color reaction. Although PVP having an average molecular weight of 24,000 g/mol shows a color reaction (entry 5), differentiation is very difficult in a low concentration range. If a polymer having an average molecular weight of about 360,000 g/mol is used, a green-blue color is obtained already with 0 mg/ml of phosphate (entry 7). The color series with PVP K40 ($M_w$=40,000 g/mol, entry 6) shows the best distinguishability. A mixture of PVP K40 and K90 (entry 8) yields no improvement of the color series. Although the copolymers PVA-Co-PVP (3:7 and 7:3, entries 9 and 10) show a color reaction, it is also weaker as compared to PVP K40. Luviskol (entry 11) is a caprolactam, and no color reaction takes place.

5. Comparative Test with Variation of the Solid Acid

A low pH is required for the reaction of molybdatophosphoric acid to form molybdenum blue. In order to establish the optimum acid, 13 different acids were tested. The test strips were prepared in accordance with Example 1 and immersed into solutions with an orthophosphate content of 0.25, 0.5, 1.0, 3.0 and 5.0 mg/l and into a phosphate-free solution for testing, and the color change of the test strips was determined. The results are represented in the Table in FIG. 5.

Different acid classes were tested. The carboxylic acids oxalic acid and tartaric acid (entries 1 and 2) do not yield a color reaction. In contrast, derivatives of amidosulfuric acid yield a color reaction for the determination of phosphate. The test paper shows the best color series with cyclamic acid (entry 3). Test papers in which methylamidosulfuric acid (entry 4) or amidosulfuric acid (entry 5) are used exhibit a lower sensitivity as compared to cyclamic acid (color reaction from 3 or 1 mg/l of phosphate, respectively, as compared to 0.5 mg/l of phosphate). Further, systems with MOPS, MES and polystyrenesulfonic acid in combination with hydrochloric acid show a very weak color reaction (entries 6-8). Also, the combination of cyclamic acids with other acids yields no improvement. For example, p-toluenesulfonic acid (entry 10) or polymers with acid functionality, such as polyacrylic acid (entry 9) or polystyrenesulfonic acid (entry 11), are tested. Acids that can also function as reducing agents (i.e., ascorbic acid, entry 12) are also tested, but without any considerable success. Cyanuric acid in combination with cyclamic acid (entry 13) cannot be tested because of solubility problems.

6. Comparative Test with Variation of the Reducing Agents

The presence of a reducing agent is indispensable for the color reaction. In order to establish the optimum reducing agent or the optimum combination of reducing agents, a total of 23 different devices were prepared and tested in two test series. The test strips were prepared in accordance with Example 1 and immersed into solutions with an orthophosphate content of 0.25, 0.5, 1.0, 3.0 and 5.0 mg/l and into a phosphate-free solution for testing, and the color change of the test strips was determined. The results are represented in the Tables in FIGS. 6 and 7.

The Table in FIG. 6 summarizes the tested reducing agents of the first test series. In addition to common reducing agents, such as ascorbic acid (entry 4), leuko bases (entries 1-3) are also tested as chromogenic reducing agents, which are supposed to be converted to the chromogen upon oxidation and thus enhance the color reaction. While ascorbic acid, syringaldazine and vanillinazine (entry 5), aminophenol (entry 6) or zinc (entry 7) do not provoke a color reaction, leuko dyes show a color reaction, above all leuko Bindschedler's green (LBG). Because of the green color of the LBG and the blue color of molybdenum blue, the test pad appears green-blue in the presence of phosphate. Further, combinations of LBG with other reducing agents are tested to ensure a fast and complete reduction. Although a color reaction is obtained in combination with another leuko dye, such as benzoyl leuko methylene blue (entry 10), the best result can be obtained with the combination of LBG and TMB (entry 8). Combinations with ascorbic acid (entry 9), phenylenediamines (entries 11-13) or o-toluidine (entry 14) show a color series only from 1 or 3 mg/l of phosphate. A sensitivity of up to 0.5 mg/l of phosphate is possible. Leuko malachite green (entry 2) and leuko crystal violet (entry 3) also produces a corresponding color reaction with TMB, but this is also weaker as compared to LBG and TMB.

The Table in FIG. 7 summarizes the tested reducing agents of the second test series. In addition to leuko Bindschedler's green (LBG, entry 1), 3,3',5,5'-tetramethylbenzidine (TMB, entry 2) also yields a color reaction. The combination of the two reducing agents (entry 3) yields the best color reaction and the best possible color grading in the concentration range of 0-5 mg/l of phosphate. A sensitivity of 0.25 mg/l of phosphate is possible. The combination of LBG with other leuko bases, such as leuko malachite green (entry 4) or leuko crystal violet (entry 5) does not yield a better color grading. Although LBG in combination with 1,3-phenylenediamine (entry 6) yields a color reaction, it does so only from about 0.5 mg/l of phosphate. Also, if 1,3-phenylenediamine is replaced by 4,4'-methylene-N,N-bis(dimethylaniline) (MDA, entry 7), a very good color grading can be achieved. This is all in all a bit lighter as compared to the combination of LBG and TMB.

Leuko malachite green (entry 8) and leuko crystal violet (entry 9) in combination with TMB also yield a color series. The sensitivity is around 0.5 mg/l of phosphate, and the distinction becomes difficult from 3.0 mg/l of phosphate.

LIST OF REFERENCE SYMBOLS 1 test device
2 plastic rod
3 support matrix

Further variants of the invention and their implementation are evident to the skilled person from the above disclosure, the Figures and the claims.

Terms used in the claims such as "comprise", "have", "include", "contain" and the like do not exclude further elements or steps. The use of the indefinite article does not exclude a plural. An individual device can execute the functions of several units or means as mentioned in the claims. Reference symbols stated in the claims are not to be considered as limitations of the agents and steps employed.

The invention claimed is:

1. A test device for determining the concentration of inorganic phosphate in a liquid sample, wherein said test device contains a support matrix serving as a support for the liquid sample, detection reagents and a detection reaction, wherein said support matrix comprises:
   a) at least one molybdate salt;
   b) at least one acid that is solid at room temperature;
   c) polyvinyl pyrrolidone (PVP) K40; and
   d) a combination of at least two different chromogenic reducing agents.

2. The test device according to claim 1, wherein said molybdate salt is selected from a group consisting of ammonium molybdate, sodium molybdate, calcium molybdate, and potassium molybdate.

3. The test device according to claim 1, wherein said at least one solid acid is selected from a group consisting of methylamidosulfonic acid, amidosulfonic acid, and cyclamic acid.

4. The test device according to claim 1, wherein said at least two different chromogenic reducing agents are selected from a group consisting of leuko Bindschedler's green (LBG), leuko malachite green (LMG), leuko crystal violet (LKV), 3,3',5,5'-tetramethylbenzidine (TMB), benzoyl-leuko-methylene blue, 4,4'-methylene-N, N-bis(dimethylaniline) (MDA), 1,2-phenylenediamine, 1,3-phenylenediamine, and 1,4-phenylenediamine.

5. The test device according to claim 4, wherein said test device has a combination of exactly two chromogenic reducing agents being one of the following combinations:
   a) LBG and TMB
   b) LBG and benzoyl-leuko-methylene blue
   c) LBG and 1,3-phenylenediamine
   d) LBG and MDA
   e) LBG and LMG
   f) LBG and LKV
   g) LMG and TMB, or
   h) LKV and TMB.

6. The test device according to claim 1, wherein said support matrix is a liquid-absorbing material selected from a group containing filter paper, non-woven, glass fiber, porous polymer material made of polysulfone, polyester, nylon, nitrocellulose, PVDF, polycarbonate.

7. The test device according to claim 6, wherein said non-woven consists of polyester (PES) and/or viscose (CV).

8. The test device according to claim 6, wherein said non-woven is a mechanically and/or thermally bonded non-woven fabric.

9. The test device according to claim 1, wherein the test device comprises a test strip with a support matrix that includes:
 a) cyclamic acid
 b) PVP K40
 c) ammonium molybdate
 d) leuko Bindschedler's green
 e) 3,3',5,5'-tetramethylbenzidine.

10. The test device according to claim 1, wherein the test device is designed as a test strip, test rod or test tape, and/or can be included in an integrated test system.

11. A test method for determining the concentration of orthophosphate in a liquid sample using the test device according to claim 1, comprising:
 soaking the support matrix with the liquid sample;
 removing any excess sample material from the support matrix; and
 visually detecting a color value of the support matrix.

12. A method for enhancing the sensitivity of a test device comprising:
 providing a test device according to claim 1.

13. The test device according to claim 8, wherein said non-woven fabric has a water absorption coefficient of from 500 to 1000 kg/m² √h.

14. The test method according to claim 11, wherein soaking the support matrix with the liquid sample comprises dipping the support matrix in the liquid sample.

15. The test method according to claim 11, further comprising shaking off or stripping off excess liquid sample.

16. The test method according to claim 11, wherein the test device comprises a test strip, and wherein the method further comprises incubating the test strip for at least 5 seconds.

17. The test method according to claim 16, wherein the test strip is incubated at room temperature.

18. The test method according to claim 11, wherein visually detecting the color value of the support matrix comprises comparing the support matrix with a color standard.

19. The method according to claim 12, wherein said test device has a combination of exactly two chromogenic reducing agents being one of the following combinations:
 a) LBG and TMB
 b) LBG and benzoyl-leuko-methylene blue
 c) LBG and 1,3-phenylenediamine
 d) LBG and MDA
 e) LBG and LMG
 f) LBG and LKV
 g) LMG and TMB, or
 h) LKV and TMB.

* * * * *